United States Patent [19]

Josey

[11] Patent Number: 4,683,091

[45] Date of Patent: Jul. 28, 1987

[54] PROCESS FOR THE NUCLEOPHILIC SUBSTITUTION OF UNACTIVATED AROMATIC AND HETEROAROMATIC SUBSTRATES

[75] Inventor: Alden D. Josey, Wilmington, Del.

[73] Assignee: E. I. Du Pont de Nemours and Company, Wilmington, Del.

[21] Appl. No.: 773,633

[22] Filed: Sep. 9, 1985

Related U.S. Application Data

[63] Continuation-in-part of Ser. No. 481,874, Apr. 11, 1983, which is a continuation-in-part of Ser. No. 378,993, May 17, 1982.

[51] Int. Cl.$^4$ .................. C07C 143/70; C07C 149/32
[52] U.S. Cl. ............................... 260/543 R; 568/56; 568/57; 568/65; 568/66; 568/656
[58] Field of Search ............... 260/543 R; 568/56, 57, 568/65, 66

[56] References Cited

U.S. PATENT DOCUMENTS 4,287,125  9/1981  Soula ..................................... 568/57

OTHER PUBLICATIONS

Sam, Donnie J. et al., *J. Am. Chem. Society* vol. 96 (1974) pp. 2252–2253.
Takeda, Nobuyuki et al., *Chemical Abstracts* vol. 88 (1978) #38,322q.
Asahi–Dow, Ltd. *Chemical Abstracts* vol. 94 (1981) #209,511c.

*Primary Examiner*—Paul J. Killos
*Assistant Examiner*—L. Hendriksen

[57] ABSTRACT

The nucleophilic substitution upon unactivated monocyclic or polycyclic aromatic or heteroaromatic substrates bearing suitable leaving groups can be achieved by catalyzing the substitution of said leaving groups by an anionic nucleophile with a cyclic or acyclic polydentate chelating ligand. Specific products of this reaction can be used in preparing sulfonylurea herbicides.

8 Claims, No Drawings

PROCESS FOR THE NUCLEOPHILIC SUBSTITUTION OF UNACTIVATED AROMATIC AND HETEROAROMATIC SUBSTRATES

RELATED APPLICATION

This application is a continuation-in-part of my copending application U.S. Ser. No. 481,874, filed Apr. 11, 1983, which is a continuation-in-part of my copending application U.S. Ser. No. 378,993, filed May 17, 1982.

BACKGROUND OF THE INVENTION

This invention relates to a new process for achieving nucleophilic substitution reactions on unactivated aromatic rings bearing appropriate leaving groups. The invention further relates to such substitution reactions by anionic nucleophiles under catalysis by a cyclic or acyclic polydentate chelating ligand.

Substituted aromatic compounds comprise a vast segment of organic chemistry. Their importance as products and intermediates ranges across the entire field of chemical manufacturing activity. Novel means for preparing substituted aromatic compounds which involve lower costs for energy, raw materials, and processing will have significant beneficial economic impact in wide areas of the chemical processing industry. In particular, improved processes for manufacture of aromatic derivatives with herbicidal and other biochemical activity offer possibilities for improved performance in production of food grains and other crops.

Few examples of nucleophilic substitutions of unactivated aromatic substrates are reported in the literature. Chemical experience clearly shows that in cases where a potential leaving group on an aromatic ring is not activated in some way, the attack of reagents that donate an electron pair in chemical reactions, i.e., nucleophiles, does not occur or is very sluggish.

In cases where such reactions are performed, they typically involve special solvents, or unusual catalysts, or forcing conditions of high temperature, or all of these. Often, the application of such extreme conditions leads to molecular rearrangements of the substrates and to mixtures of products.

SUMMARY OF THE INVENTION

It has now been found that the nucleophilic substitution upon unactivated monocyclic or polycyclic aromatic or heteroaromatic substrates bearing suitable leaving groups can be achieved by catalyzing the substitution of said leaving groups by an anionic nucleophile with a cyclic or acyclic polydentate chelating ligand. This new process is advantageous in that it provides a means for achieving such useful substitution reactions in high yields, conversions and selectivity, in inexpensive solvents such as hydrocarbons, without special metal-containing catalysts, and without the requirement of extreme temperature and pressure conditions.

In one embodiment of this invention, the compound ortho-dichlorobenzene is converted to ortho-chlorophenyl alkyl sulfide which can then be converted to a number of useful herbicidal compounds.

DETAILED DESCRIPTION OF THE INVENTION

The nucleophilic substitution reaction of this invention can be illustrated schematically by the following reaction:

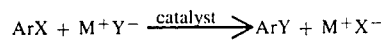

where
- Ar is the unactivated optionally substituted aromatic or heteroaromatic substrate,
- X is the leaving group,
- Y is the anionic nucleophile, and
- M is a cationic counterion.

The catalyst used in this process is a cyclic or acyclic polydentate ligand which is capable of solvating and complexing the cation (M) in association with the anionic nucleophile (Y). These catalysts are molecules with multiple binding sites for coordinating with a cation. The catalyst can have any number of binding sites, the preferred number of sites and the spacing of those sites in the molecule being dependent upon the nature of the cation with which it is to coordinate.

A wide variety of polydentate ligands are known in the art. They generally have multiple functionalities such as ether, amine and/or thioether groups. Examples of cyclic ligands are the crown ethers and their fused-ring derivatives, and other cyclic cooligomers of glycols. Crown ethers are a well known class of compounds, the preparation and identity of which are fully described in U.S. Pat. No. 3,687,978. See also *Angew. Chem.*, 84, 16 (1972) and *Phase Transfer Catalysts, Principles and Techniques*, C. M. Starks and C. Liotta, Ch. 3. Academic Press (1978). Crown ethers are macro-monocyclic polyethers and may be generally defined as being rings containing repeating $(-X-CH_2-CH_2-)_n$ units. For the cases wherein $X=O$, the repeating unit is ethyleneoxy. If the carbon portion is one carbon shorter the repeating unit would be methyleneoxy. If longer carbon chains are involved, the CH—CH interactions will exert an effect on the overall conformation of the macro ring.

The generic name "crown" is suggested by the similarity of the molecular models to a regal crown and by the abilities of these compounds to "crown" cations by complexation. The smallest value of n which fits the above definition is 2 as in 1,4-dioxane; however, for the purposes of this invention, useful crown ethers are those in which n is 4 or more. The crown compound designated 18-crown-6 is 1,4,7,10,13,16-hexaoxacyclooctadecane. 18 represents the total number of atoms in the ring, crown is the class name and 6 is the total number of hetero atoms in the ring portion of the macrocycle. The principal variation in X according to the above formula is to substitute NH or NR for the oxygen atoms. Sulfur and phosphorous atoms and methylene units have also been substituted for oxygen. These are only representative examples of the many varieties possible. For a more comprehensive description of crown ether structures, reference is made to the above-mentioned U.S. Pat. No. 3,687,978 which also gives a detailed description of how to synthesize such molecules. Exemplary crown compounds are 1,4,7,10,13,16-hexaoxacyclooctadecane (18-crown-6); 15-crown-5; and fused-ring derivatives of crown compounds such as dibenzo-18-crown-6; monobenzo-15-crown-5; dicyclohexyl-18-crown-6; monocyclohexyl-15-crown-5; dibenzo-24-crown-8 and dicyclohexyl-24-crown-8. Cyclic co-oligomers of other glycols, e.g. where the repeating unit in the above formula is propyleneoxy, can also be used in this invention. "Crypt" compounds, the three-dimensional macrocyclic counterparts of the crown compounds, are also useful polydentate ligands. The term "crown ethers" as used herein is intended to encompass all of the variations discussed above.

Acyclic ligands include such polyethers as the polyethyleneglycols, polyethyleneglycol ethers and copolymers of ethylene oxide and tetrahydrofuran. Polyethylene glycols (PEGs) are open-chain, linear polymers of ethylene oxide with the general formula $H(OCH_2CH_2)_nOH$ in which n represents the number of ethylene oxide units in the polymer chain. Industrial PEGs are designated by a number that expresses the average molecular weight of a mixture of polymers. For example, PEG 400 is a mixture of polyethylene oxides of average molecular weight 400 in which the number of ethylene oxide units in the chain ranges from 3 to 17. For further examples, see "Carbowax ®, Polyethylene Glycols," a technical bulletin of the Union Carbide Company.

Certain commercially-available derivatives of PEGs in which a methyl group replaces the hydrogen atom at one end of the polymer chain are designated as methoxy PEGs. For example, methoxy PEG 350 is a mixture of methoxy PEGs of average molecular weight 350 in which the number of ethylene oxide units in the chain is about 2 to 14. Both the PEGs and methoxy PEGs are effective catalysts for nucleophilic aromatic substitution reactions as described herein. In addition, certain less readily available derivatives in which both terminal hydrogen atoms of the polymer chain are replaced by methyl groups are also effective catalysts. Polypropylene glycols, another type of derivative of the PEGs, should also be effective catalysts for use in this invention.

These open-chain polyether compounds function as catalysts for nucleophilic substitution reactions by solvating and complexing metal ions in a way similar to that of the cyclic crown ether compounds. Members of this general class of "open-chain crown compounds" are designated "podands", which includes all ligands possessing characteristics of an open-chain oligoether or consisting of chains bearing heteroatoms in a particular array. Oxygen atoms in the polymer chain may be replaced by other atoms, for example, N or S, to give polymeric ligands that are useful catalysts. Examples include polyethyleneimine,$-(CH_2CH_2NH)_n-$ and molecules containing multiple polyether and polythioether chains. The term "acyclic polyether" as used herein is intended to encompass all of the variations discussed above.

The preferred catalysts for use in this invention, for reasons of efficiency and economy, are polyethylene glycol ethers having an average molecular weight in the range of about 200–20,000, more preferably 300–6,000 and most preferably 300–2,000.

The polydentate ligand serves to catalyze the nucleophilic substitution reaction of this invention and therefore need not be used in stoichiometric quantities. It is expected that the use of the catalyst in an amount as little as one percent by weight based on the anionic nucleophile will suffice to catalyze the reaction, and even smaller quantities may be operative. There is essentially no upper limit on the amount of catalyst utilized although economic considerations may preclude the use of great excesses of the catalyst. Generally, the use of the catalyst in an amount of about 1 to 50% by weight based on the anionic nucleophile is preferred. More preferred is the use of about 10 to 15% by weight of catalyst.

The aromatic or heteroaromatic substrates may be monocyclic, for example, benzene, thiophene or pyridine, or polycyclic, for example, naphthalene, quinoline, azulene, anthracene, or carbazole, or optionally-substituted derivatives of these. The heteroaromatics are those containing one or more heteroatoms such as nitrogen, sulfur or oxygen or a combination thereof. One skilled in the art would be well aware of the variety of aromatic and heteroaromatic substrates available. See, for example, *CRC Handbook of Chemistry and Physics*, 60th Ed., (1980), pp. C-1 to C-58.

Preferred aromatic and heteroaromatic substrates are unactivated benzene, naphthalene, pyridine, thiophene, pyrimidine, furan and quinoline. More preferred is unactivated benzene, e.g., the dichlorobenzenes, and most preferred is ortho-dichlorobenzene.

An important aspect of this invention is the fact that the optionally-substituted aromatic or heteroaromatic substrate is unactivated. This term is known in the art and describes a substrate which, for one reason or another, is relatively unreactive toward nucleophilic substitution. From the extensive literature on nucleophilic aromatic substitution, it is recognized that certain substituents in certain positions on the aromatic ring will have the effect of activating nucleophilic substitution on the substrate while others will have the opposite effect. Similarly, the position of the potential leaving group in relation to the hetero atom(s) in a heteroaromatic substrate can affect the activity of the substrate towards nucleophilic substitution. See, for example, *Chem. Rev.*, 49, 273 (1951); J. March, *Advanced Organic Chemistry: Reactions, Mechanisms and Structure*, McGraw-Hill, New York (1968), pp. 494–499; and J. Miller, *Aromatic Nucleophilic Substitution*, Elsevier, New York, 1968.

In order to define more precisely the term unactivated as used herein and as it applies the benzene derivatives, reference is made to the Hammett substituent constants. These substituent constants, represented by the term $\sigma$, are a parameter of the Hammett Equation, well known to those skilled in the art. See, e.g., Hirsh, "Concepts in Theoretical Organic Chemistry," Allyn and Bacon, 1974, p. 108–113. The constant $\sigma$ is characteristic of a substituent and represents the ability of the substituent group to attract or repel electrons from an aromatic ring, as compared to a hydrogen atom. Positive values of $\sigma$ indicate that a substituent withdraws electrons from a benzene ring as compared to hydrogen, whereas negative values indicate electron donation. Since the scale used to define $\sigma$ is logarithmic, the differences in reactivity are even greater than the number itself suggests. The following table lists Hammett constants for a number of substituents (from Jaffe, *Chem. Revs.*, 53, 191 (1953)).

TABLE I

| Hammett Substituent Constants: $\sigma_m$ and $\sigma_p$ | | |
| --- | --- | --- |
| Substituent | $\sigma_m$ | $\sigma_p$ |
| $CH_3$ | −0.069 | −0.170 |
| $C_2H_5$ | −0.043 | −0.151 |
| $C_3H_7$ | | −0.126 |
| $CH(CH_3)_2$ | | −0.151 |
| $C_4H_9$ | | −0.161 |
| $CH_2CH(CH_3)_2$ | | −0.115 |
| $CH(CH_3)C_2H_5$ | | −0.123 |

TABLE I-continued

Hammett Substituent Constants: $\sigma_m$ and $\sigma_p$

| Substituent | $\sigma_m$ | $\sigma_p$ |
|---|---|---|
| C(CH$_3$)$_3$ | −0.120 | −0.197 |
| (CH$_2$)$_2$CH(CH$_3$)$_2$ | | −0.225 |
| C(CH$_3$)$_2$C$_2$H$_5$ | | −0.190 |
| CF$_3$ | 0.415 | 0.551 |
| CH$_2$CN | | 0.007 |
| CH$_2$CH$_2$COOH | −0.027 | −0.066 |
| OH | −0.002 | −0.357 |
| OCH$_3$ | 0.115 | −0.268 |
| OC$_2$H$_5$ | 0.150 | −0.250 |
| OC$_3$H$_7$ | | −0.268 |
| OCH(CH$_3$)$_2$ | | −0.286 |
| OC$_4$H$_9$ | | −0.320 |
| OC$_5$H$_{11}$ | | −0.340 |
| O(CH$_2$)$_5$CH(CH$_3$)$_2$ | | −0.265 |
| OCH$_2$C$_6$H$_5$ | | −0.415 |
| OC$_6$H$_5$ | | −0.028 |
| O$^-$ | −0.708 | −0.519 |
| NH$_2$ | −0.161 | −0.660 |
| NHCH$_3$ | −0.302 | −0.592 |
| NHC$_2$H$_5$ | −0.240 | |
| NHC$_4$H$_9$ | −0.344 | |
| N(CH$_3$)$_2$ | −0.211 | −0.600 |
| NHCOCH$_3$ | | −0.015 |
| NHCOC$_6$H$_5$ | −0.217 | −0.078 |
| NHNH$_2$ | −0.020 | −0.550 |
| NHOH | −0.044 | −0.339 |
| COOH | 0.355 | 0.265 |
| COOCH$_3$ | 0.315 | |
| COOC$_2$H$_5$ | 0.398 | 0.522 |
| COOC$_4$H$_9$ | | |
| COOCH$_2$C$_6$H$_5$ | | |
| CONH$_2$ | 0.280 | |
| CHO | 0.355 | 0.216 |
| COCH$_3$ | 0.306 | 0.516 |
| COC$_6$H$_5$ | | 0.459 |
| CN | 0.678 | 0.628 |
| COO$^-$ | 0.104 | 0.132 |
| NO$_2$ | 0.710 | 0.778 |
| NO | | 0.123 |
| F | 0.337 | 0.062 |
| Cl | 0.373 | 0.227 |
| Br | 0.391 | 0.232 |
| I | 0.352 | 0.276 |
| SCH$_3$ | 0.144 | −0.047 |
| SOCH$_3$ | 0.551 | 0.567 |
| SO$_2$CH$_3$ | 0.647 | 0.728 |
| SCN | | 0.699 |
| SeCN | | 0.664 |
| B(OH)$_2$ | 0.006 | 0.454 |
| Si(CH$_3$)$_3$ | −0.121 | −0.072 |
| C$_6$H$_5$ | 0.218 | 0.009 |
| N=NC$_6$H$_5$ | | 0.640 |
| CH=CHC$_6$H$_5$ | 0.141 | |
| AsO$_3$H$^-$ | | −0.019 |
| PO$_3$H$^-$ | 0.228 | 0.238 |
| SO$_3^-$ | | 0.381 |
| SO$_2$NH$_2$ | | 0.621 |
| 3,4-(CH$_2$)$_3$* | | −0.259 |
| 3,4-(CH$_2$)$_4$* | | −0.477 |
| 3,4-(CH)$_4$* | | 0.170 |
| 3,4-CH$_2$O$_2$* | | −0.159 |

*fused-ring systems.

The value for $\sigma_m$ is the Hammett constant for the substituent when it is located in the meta-position to the leaving group. Similarly the value $\sigma_p$ is the Hammett constant for the substituent when it is located in the para-position to the leaving group. Hammett values for ortho-substituents are not readily available; however, for the purpose of this invention, the Hammett value, $\sigma_o$ for a substituent in the ortho-position to the leaving group will be equal to the Hammett value for the same substituent in the para-position, $\sigma_p$.

For the purposes of this invention, the Hammett values are a measure of the activating influence of a substituent on aromatic nucleophilic substitution. An unactivated benzene derivative is defined as one in which the algebraically-combined $\sigma$ values for the substituents on the benzene ring (other than the leaving group) do not exceed +0.455. For example, the Hammett value for ortho-dichlorobenzene would be +0.227, and this compound would thus be "unactivated" according to this invention. In fact, ortho-dichlorobenzene is cited in many references as being unactivated toward the type of nucleophilic substitution reactions described herein. See, e.g., J. Org. Chem. 44, 2642 (1979).

For certain tri- or higher-substituted benzenes, the substitution patterns will result in multiple values of combined $\sigma$ values. In these cases, the lowest sum is to be used to determine whether the substrate is unactivated according to this invention. For example, in 1,2,3-trichlorobenzene, if the 2-chlorine is the leaving group, the combined $\sigma$ values of the two remaining ortho-chlorine atoms is 0.227 ($\sigma_p$)+0.227 ($\sigma_p$)=0.454. If the 1-chlorine is the leaving group the combined $\sigma$ values of the two remaining chlorine atoms, one ortho- and one meta-, is 0.227 ($\sigma_p$)+0.373 ($\sigma_m$)=0.600. In this case, the lower combined $\sigma$ value, 0.454, is determining, and this benzene derivative is unactivated according to this invention.

Table II lists representative aromatic substrates which are unactivated and thus useful as starting materials according to this invention. Of course, there are many other compounds besides those listed in Table II which could be useful.

TABLE II

Y—C$_6$H$_4$—(R)$_n$

| Y | R$_1$ | R$_2$ | R$_3$ | R$_4$ | R$_5$ | Sum of $\sigma$ |
|---|---|---|---|---|---|---|
| Cl | 2-Cl | H | H | H | H | 0.227 |
| Cl | 2-Cl | 6-Cl | H | H | H | 0.454 |
| Cl | 2-OCH$_3$ | H | H | H | H | −0.268 |
| Cl | 2-SCH$_3$ | H | H | H | H | −0.047 |
| Cl | 2-SCH$_2$CH$_2$CH$_3$ | H | H | H | H | — |
| Cl | 2-CH$_3$ | H | H | H | H | −0.170 |
| Cl | 3-CH$_3$ | H | H | H | H | −0.069 |
| Cl | 2-CH$_3$ | 3-Cl | H | H | H | 0.203 |
| Cl | H | H | H | H | H | 0.0 |
| Cl | 3,4-(CH)$_4$ | H | H | H | H | 0.170 |
| NO$_2$ | 2-OCH$_3$ | H | H | H | H | −0.268 |
| NO$_2$ | 3-OCH$_3$ | H | H | H | H | 0.115 |
| NO$_2$ | 2-Cl | H | H | H | H | 0.227 |
| NO$_2$ | 2-COOH | H | H | H | H | 0.265 |
| OSO$_2$CH$_3$ | H | H | H | H | H | 0.0 |
| OSO$_2$CH$_3$ | 2-OCH$_3$ | H | H | H | H | −0.268 |
| OSO$_2$CH$_3$ | 2-Cl | H | H | H | H | 0.227 |
| OP(O)(OCH$_3$)$_2$ | H | H | H | H | H | 0.0 |
| OP(O)(OCH$_3$)$_2$ | Cl | H | H | H | H | 0.227 |
| O—P(O)OCH$_3$ (CH$_3$) | Cl | H | H | H | H | 0.227 |
| O—P(O)OCH$_3$ (CH$_3$) | H | H | H | H | H | 0.0 |

Tables I and II are not all-inclusive, but, based on these tables, on the foregoing discussion, and on information readily available to one skilled in the art, it will be easy to determine if a given benzene derivative is "unactivated" according to this invention.

The Hammett equation is not directly applicable to heteroaromatic substrates. For the purposes of this invention, an unactivated heteroaromatic substrate is one which is not substituted ortho- or para- to the leaving group by activating substituents such as nitro, alkylsulfonyl, trialkylammonium, cyano or acyl. Further, for six-membered nitrogen-containing heterocycles, the leaving group may not be ortho- or para- to a ring nitrogen. Examples of unactivated heteroaromatic substrates according to this invention are presented in Tables III–VI.

TABLE III

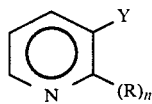

n = 1-4

| Y | $R_1$ | $R_2$ | $R_3$ | $R_4$ |
| --- | --- | --- | --- | --- |
| 3-Cl | H | H | H | H |
| 3-Cl | 2-CH$_3$ | H | H | H |
| 3-Cl | 2-CH$_3$ | 6-CH$_3$ | H | H |
| 3-Cl | 6-CH$_3$ | H | H | H |
| 3-Cl | 4-CH$_3$ | H | H | H |

TABLE IV

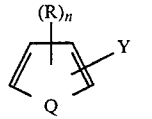

Q = O or S
n = 1 to 3

| Y | $R_1$ | $R_2$ | $R_3$ | Q |
| --- | --- | --- | --- | --- |
| 3-Cl | H | H | H | O |
| 3-Cl | H | H | H | S |
| 3-Cl | 5-CO$_2$CH$_3$ | H | H | O |
| 3-Cl | 5-CO$_2$CH$_3$ | H | H | S |
| 2-Cl | 5-CO$_2$CH$_3$ | H | H | O |
| 2-Cl | 5-CO$_2$CH$_3$ | H | H | S |

TABLE V

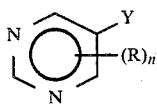

n = 1 to 3

| Y | $R_1$ | $R_2$ | $R_3$ |
| --- | --- | --- | --- |
| 5-Cl | H | H | H |
| 5-Cl | 2-CH$_3$ | H | H |
| 5-Cl | 4-CH$_3$ | H | H |
| 5-Cl | 2-CH$_3$ | 4-CH$_3$ | H |

TABLE VI

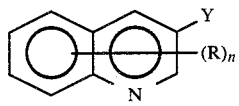

n = 1 to 6

| Y | $R_1$ | $R_2$ | $R_3$ | $R_4$ | $R_5$ | $R_6$ |
| --- | --- | --- | --- | --- | --- | --- |
| 3-Cl | H | H | H | H | H | H |
| 3-Cl | 2-CH$_3$ | H | H | H | H | H |
| 3-Cl | 4-CH$_3$ | H | H | H | H | H |
| 6-Cl | H | H | H | H | H | H |
| 3-Cl | 6-CH$_3$ | H | H | H | H | H |
| 3-Cl | 6-OCH$_3$ | H | H | H | H | H |
| 3-Cl | 6-SCH$_3$ | H | H | H | H | H |
| 3-Cl | 6-CH$_3$ | 7-CH$_3$ | H | H | H | H |

TABLE VI-continued

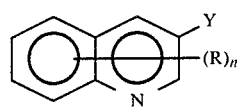

n = 1 to 6

| Y | $R_1$ | $R_2$ | $R_3$ | $R_4$ | $R_5$ | $R_6$ |
| --- | --- | --- | --- | --- | --- | --- |
| 3-Cl | 6-Cl | 7-Cl | H | H | H | H |

The aromatic or heteroaromatic substrate is also substituted with a suitable leaving group, the leaving group being any moiety which is capable of being displaced in a nucleophilic substitution reaction. Examples of suitable leaving groups include, but are not limited to, halogen, nitro, sulfonates, phosphonates, phosphinates and phosphates. In the preferred embodiments of this invention, the leaving group is a halogen, more preferably, chlorine.

The anionic nucleophile in the process of this invention is a molecule having a pair of electrons to donate to the aromatic or heteroaromatic substrate to form a covalent bond. Examples of such nucleophiles include, but are not limited to, the following:

sulfhydryl, $-SH$
disulfide, $-SS-$
mercaptides, $-SR_3$
thiocyanate
xanthate
alkoxides, $-OR_4$
amine anions, $-R_5R_6N$
carbanions, $-R_7R_8R_9C$ where
$R_3$ and $R_4$ are alkyl, aryl or aralkyl;
$R_5$ and $R_6$ are independently H, alkyl or aryl;
$R_7$ is acyl, carboalkoxy, nitro or cyano; and
$R_8$ and $R_9$ are independently H, alkyl, aryl, acyl, carboalkoxy, nitro or cyano.

The cation associated with the anionic nucleophile may be an alkali metal, an alkaline earth metal, transition metal, or optionally alkylated ammonium or phosphonium ion. In the preferred embodiment, it is an alkali metal, and more preferably potassium.

Virtually any solvent compatible with the anionic nucleophile may be used, including aromatic and aliphatic hydrocarbons, ethers, nitriles, or nitrobenzene compounds. Choice of solvent is not critical. Optionally, excess aromatic substrate may function as solvent. Aromatic hydrocarbon solvents or excess substrate are preferred.

The temperature of reaction is not critical and will vary widely according to the aromatic or heteroaromatic substrate, the nucleophile, the solvent, the catalyst, and the reaction time desired. In many instances, temperatures of 100°-200° C. are preferred.

The pressure at which the process may be operated may vary widely, and ambient pressure is generally preferred. In most cases, the order of mixing the various components will not be important.

The nucleophilic substitution process of this invention can be described in more detail by reference to the preferred embodiment of the invention. In this preferred embodiment, one of the chlorine atoms in ortho-dichlorobenzene is substituted with an alkyl mercaptide (lower alkyl, e.g. one to six carbon atoms, preferably potassium n-propylmercaptide) as illustrated in the following reaction scheme:

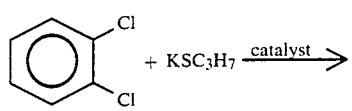

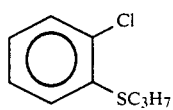

The preferred catalyst for use in this process is an acyclic polyethylene glycol with average molecular weight of 400. Suitable solvents include hydrocarbons such as toluene and xylene; however, in a more preferred embodiment, ortho-dichlorobenzene serves as both reactant and solvent. The use of ortho-dichlorobenzene as solvent is especially convenient as it is possible to proceed to the synthetic sequence described below without having to first remove solvent.

The reaction of ortho-dichlorobenzene with potassium n-propylmercaptide shown above is carried out by combining the reagents, solvent (in the preferred case, ortho-dichlorobenzene), and catalyst in any sequence. The mixture is heated, and the progress of the reaction is monitored by gas chromatography.

The temperature is not critical, and acceptable reaction rates are obtained at 100° C. However, the reaction proceeds at a faster rate as the temperature is increased. Therefore, the preferred temperature range is 150°–180° C., the latter being the boiling point of ortho-dichlorobenzene. The pressure is not critical, and reactions have been carried out in glass vessels open to the atmosphere as well as in sealed autoclaves without substantially different results. It is preferred for convenience and economy to carry out the reaction in a glass vessel at atmospheric pressure at internal temperatures of 175°–180° C., under which conditions the formation of ortho-chlorophenyl n-propyl sulfide is substantially complete in 2–4 hours.

The reaction of potassium methyl mercaptides with ortho-dichlorobenzene to produce ortho-chlorophenyl methyl sulfide is also best conducted as described above.

In an additional embodiment of this invention, the o-chlorophenyl alkyl sulfide, prepared as described above, is reacted as shown in the following schemes to prepare valuable benzenesulfonyl chloride intermediates:

Scheme A

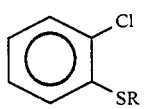

(R = lower alkyl)

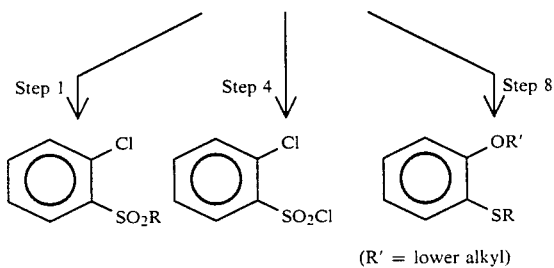

(R' = lower alkyl)

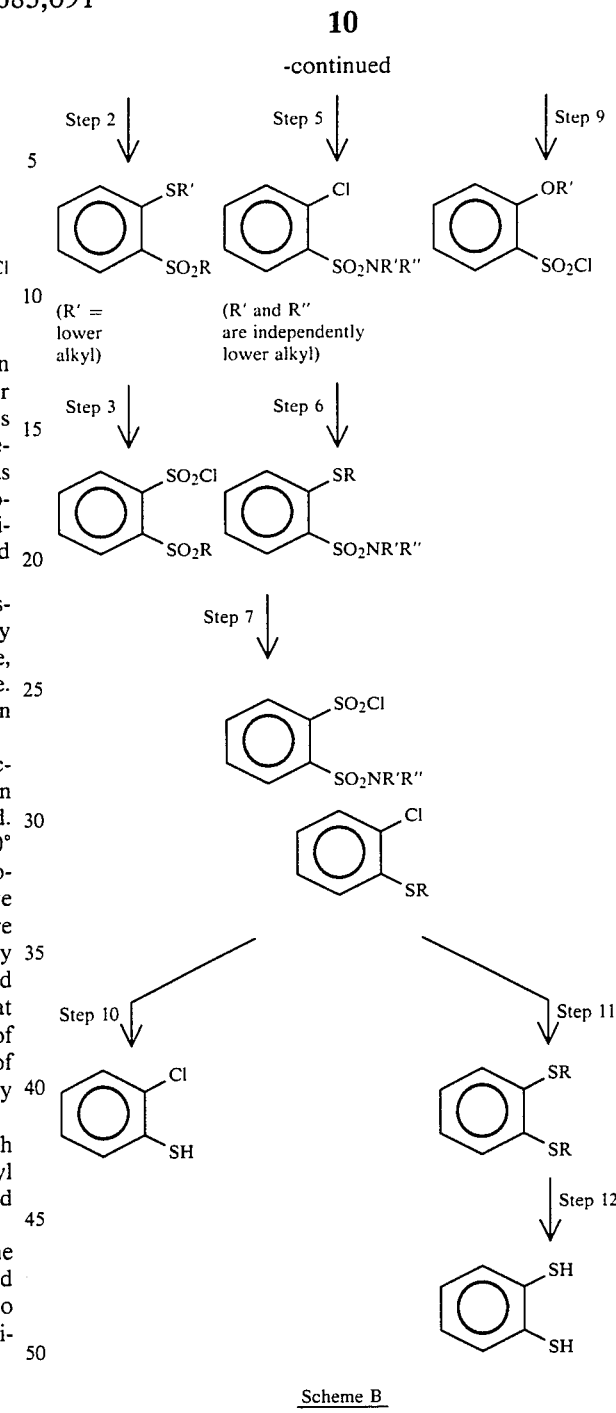

Scheme B

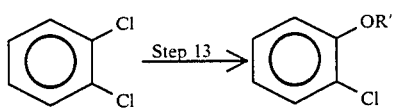

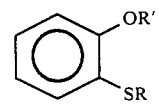

R and R' are independently lower alkyl

Step 1 of Scheme A, the oxidation of o-chlorophenyl alkyl sulfide to the corresponding sulfone, can be carried out in either of two ways:

a. By alkaline sodium hypochlorite

A solution of the sulfide in an organic solvent is stirred vigorously in contact with an immiscible aqueous solution of sodium hypochlorite (about 1 to 15%, preferably about 5%). At least two molar equivalents of hypochlorite per equivalent of sulfide are used. The formation of the sulfone and its increasing concentration in the organic phase are monitored by gas chromatography. The reaction is slightly exothermic, and no external heat is required. Pressure is not critical, and it is preferred to carry out the oxidation in a glass vessel open to the atmosphere.

The solvent may be chosen from the group of aromatic hydrocarbons (e.g., benzene, toluene, xylene), esters of carboxylic acids (e.g., ethyl acetate, amyl acetate), halogenated aliphatic compounds (e.g., methylene chloride, chloroform, carbon tetrachloride), or halogenated aromatic compounds (chlorobenzene, ortho-dichlorobenzene). A preferred solvent is ethyl acetate in which oxidation rates are significantly faster than in the other solvents cited.

b. By acidic hydrogen peroxide

A solution of the sulfide in acid such as acetic acid and, optionally, a second solvent chosen from the group listed above, but preferably ortho-dichlorobenzene, together with concentrated mineral acid such as sulfuric acid in the amount of about 0.1 to 10%, preferably about 1%, based on the weight of acetic acid present, is stirred in a glass vessel open to the atmosphere while an aqueous solution containing hydrogen peroxide in the amount of 30-70 weight %, but preferably 50%, is added.

The reaction is exothermic, and the internal temperature is preferably controlled not to exceed about 80° C. during the addition of hydrogen peroxide. Thereafter, the reaction mass is stirred for 15-60 minutes, then heated at reflux for ½ to 2 hours, preferably for 1 hour, and cooled.

The organic layer is removed and washed with water to remove acidic materials. The organic layer, which contains ortho-chlorophenyl alkyl sulfone in the theoretical amount, can be used directly in the next reaction.

The use of ortho-dichlorobenzene as the preferred solvent in the oxidation step confers upon the overall process the great practical advantage that solutions of ortho-chlorophenyl alkyl sulfide in orthodichlorobenzene, which are the direct product of the preferred embodiment of the nucleophilic substitution process described above, may be used directly in Step 1, the oxidation step, without having to isolate and purify the sulfide. As a result, manufacturing costs are reduced and physical processing is simplified.

In Step 2 of the aforementioned synthetic schemed, the ortho-chlorophenyl alkyl sulfone from Step 1 is reacted with alkyl mercaptide.

The reagents are combined in any order and heated at 50°-180° C., preferably at 100°-110° C., for 4-5 hours in a glass vessel open to the atmosphere. The formation of the product ortho-alkylthiophenyl alkyl sulfone is monitored by gas chromatography. The conversion of starting chloro compounds to sulfide is substantially complete after 5 hours.

The solvent may be an aromatic hydrocarbon (toluene, xylene) or a halogenated aromatic (chlorobenzene, ortho-dichlorobenzene). The most preferred embodiment is that in which the solvent is ortho-dichlorobenzene, since the starting chloro compound is produced in this solvent as a product of Step 1 and may be used directly in this form in Step 2.

Catalysts are not required in ortho-dichlorobenzene solvent but may be used optionally to increase the reaction rate and reduce processing time if this is desired. Preferred catalysts are polyethylene glycols and polyethylene glycol ethers in the molecular weight range of 200-20,000, preferably 300-6000, and most preferably 300-2000. Preferred catalyst concentration is 1-50%, more preferably 10-15%, by weight of the mercaptide.

The displacement reaction of Step 2 can optionally be carried out without prior formation of the alkyl mercaptide salt by using a phase transfer catalytic process. In this embodiment, the o-dichlorobenzene solution of o-chlorophenyl alkyl sulfone produced in Step 1 is stirred in contact with an immiscible aqueous solution of sodium hydroxide and a catalyst chosen from the group of tetraalkylammonium, tetralkylphosphonium and tetraalkylarsonium salts, while alkyl mercaptan is added. The immiscible layers are stirred together while the slightly exothermic reaction producing o-alkylthiophenyl alkyl sulfone proceeds without external heating. The reaction is monitored by gas chromatography and is substantially complete in four to six hours. The aqueous layer is discarded, and the organic layer is washed with water to remove residual sodium hydroxide. The ortho-dichlorobenzene solution of ortho-alkylthiophenyl alkyl sulfone may be used in the next step of the synthetic scheme as described below.

In Step 3 of the aforementioned synthetic scheme, ortho-alkylthiophenyl alkyl sulfone is chlorinated in the presence of water to produce ortho-alkylsulfonylbenzenesulfonyl chloride.

The chlorination may be carried out with or without added solvent. If solvents are used, they may be chosen from the group of lower aliphatic carboxylic acids, preferably acetic acid, or halogenated aromatics, preferably ortho-dichlorobenzene. In the preferred embodiment, the chlorination is carried out upon ortho-dichlorobenzene solutions of the sulfide, since this is the form in which the latter is obtained as the product of Step 2 above.

Water is added in the amount of 2-3, preferably 2.5, molar equivalents based on the moles of starting sulfide, and chlorine is passed in the amount of 5-6, preferably 5, molar equivalents based on the moles of starting sulfide. Temperature is not critical, but the reaction is slightly exothermic in its initial stages, and the yields of sulfonyl chloride are best when the temperature is not allowed to exceed 60° C. When the addition of chlorine is complete, the reaction mass is maintained at 60° C. for about 2 hours and then cooled. If carboxylic acid solvents are used, excess water is added, and the sulfonyl chloride separates as a crystalline solid. The product is collected by filtration and dried in air.

If, as in the preferred embodiment, ortho-dichlorobenzene is used, the organic layer is separated, washed with water to remove hydrochloric acid and other water-soluble impurities, and dried over a solid drying agent, preferably magnesium sulfate. The solvent can be removed and the sulfonyl chloride isolated as a crystalline solid, or preferably, the dry solution can be used in subsequent synthetic operations.

A second sequence of reactions begins with Step 4, in which ortho-chlorophenyl alkyl sulfide is chlorinated in the presence of water to produce ortho-chlorobenzenesulfonyl chloride.

The preferred embodiment of the chlorination reaction is carried out as described in detail in the preferred embodiment Step 3 described above. The product sulfonyl chloride is a liquid under normal temperature and pressure and can be isolated from its dry solutions in ortho-dichlorobenzene or used as the solution in subsequent synthetic operations.

Subsequent reaction with a dialkyl amine as in Step 5 produces an N,N-dialkyl-ortho-chlorobenzenesulfonamide. Any solvent suitable for the initial displacement of o-dichlorobenzene will also be operable here, and as before, ortho-dichlorobenzene is preferred. An acid acceptor is not required but may speed the reaction. Examples of useful acid acceptors include excess dialkylamine or a tertiary amine such as triethylamine or pyridine. The product may be isolated, or in those cases where no acid acceptor is used or where the salt of the acid acceptor can be removed by washing or filtration, the resulting solution of sulfonamide may be used in subsequent steps.

Displacement of chloride from the N,N-dialkyl-ortho-chlorobenzenesulfonamide with an alkyl mercaptide as in Step 6 may be accomplished using essentially the conditions described for Step 2.

Step 7 of Scheme A, oxidative chlorination of the N,N-dialkyl-ortho-(alkylthio)benzenesulfonamide produced in Step 6 to give an N,N-dialkyl-ortho-(chlorosulfonyl)benzenesulfonamide, is conducted essentially as described for Step 3. The products of Step 7 may also be named ortho-(N,N-dialkylsulfamoyl)benzenesulfonyl chlorides.

Another sequence of steps to convert ortho-chlorophenyl alkyl sulfides to useful sulfonyl chlorides begins with Step 8, displacement of chloride by an alkoxide, preferably a potassium alkoxide. Conditions here will be essentially the same as those described for reactions of ortho-dichlorobenzene with mercaptides, with two exceptions. First, in Step 8 control of temperature may be more important. For some values of SR (for example primary thioethers), displacement of R by alkoxide may compete with displacement of chloride, and using the lowest temperature (80° to 100° C.) at which chloride displacement occurs at an acceptable rate will often minimize the undesired reaction. Second, although ortho-dichlorobenzene may be an operable solvent, it is no longer preferred because it may react with alkoxide.

Step 9, oxidative chlorination of the product of Step 8 to give an ortho-alkoxybenzenesulfonyl chloride, is conducted in essentially the same way as described for Step 3.

Step 10, the cleavage of the alkyl group with formation of a mercaptan, is restricted to those cases in which R is a secondary or tertiary alkyl group, preferably the latter, e.g., tertiary butyl, and is carried out by heating the thioether (100° to 150° C.) with a strong acid, e.g., para-toluenesulfonic acid or trifluoromethanesulfonic acid until gas chromatographic analysis shows the thioether is completely consumed. Suitable solvenfts include hydrocarbons such as xylene, chlorinated aromatics such as o-dichlorobenzene, nitrobenzene, diphenyl ether, certain amides and sulfones.

Steps 11 and 12 constitute a route to ortho-benzenedithiols, a class of compounds having wide synthetic application and for which present methods of synthesis are tedious or difficult. In Step 11, repetition of the catalytic mercaptidation reaction using as substrate an ortho-chlorophenyl alkyl thioether gives ortho-alkylthiobenzenes. Since both starting material and final products are liquids, no solvent is required. However, a high-boiling aromatic hydrocarbon, ether, or other suitable solvent as previously described can be used. As shown in Step 12, the ortho-bis-alkylthiobenzenes can be cleaved by sodium metal in liquid ammonia to give the salt of the bis-thiophenol, which is known in the art (*Organic Synthesis*, Coll, Vol. V, p. 419). Acidification of the reaction mixture with solid ammonium chloride gives the ortho-dithiols. When the alkyl group R is a primary alkyl group, treatment of the bis-alkylthiobenzene with mercaptides, e.g. $KSCH_3$, affords the salt of the bis-thiophenol and a dialkylthioether. The dialkylthioether is volatile and is distilled from the reaction mixture. Acidification with mineral acids gives the ortho-dithiols. In certain cases, where the R groups are secondary or tertiary alkyl groups, cleavage to the dithiols is effected with strong acids as noted above. The bis-thioethers and bis-thiophenols prepared in this manner can be chlorinated in the presence of water, using procedures analogous to those described above for Step 3, to prepare a disulfonyl chloride.

An alternate route from ortho-dichlorobenzene to the products of Step 8 is outlined in Scheme B. The first displacement on ortho-dichlorobenzene, Step 13, is conducted with alkoxide, preferably potassium alkoxide, according to the conditions outlined for reactions of mercaptides with ortho-dichlorobenzene. Subsequent displacement of chloride by mercaptide, Step 14, to give ortho-alkoxyphenyl alkyl sulfides is conducted essentially as described for reactions of mercaptides with ortho-chlorophenyl alkyl sulfides (Step 8). Here, as in Step 8, lower temperatures may suppress a competing reaction for primary ethers, i.e., in this case cleavage of the alkyl phenyl ether, and ortho-dichlorobenzene may no longer be considered a preferred solvent. If ether cleavage occurs, the ether can be re-formed by treating the reaction mixtures with an alkyl halide, R'X, to re-alkylate the aryl oxide group formed in the cleavage reaction.

Many of the sulfonyl chlorides, prepared as described above in Schemes A and B, can be converted to a variety of highly active sulfonylurea herbicides. The sulfonyl chlorides are first converted to sulfonamides by processes well known in the art. Crossely et al., *J. Am. Chem. Soc.*, 60, 2223 (1938), for example, discusses the preparation of arylsulfonamides from ammonium hydroxide and arylsulfonyl chloride. The resulting sulfonamide is then converted to a sulfonyl isocyanate by phosgenation, a process also described in the art. See, for example, U.S. Pat. Nos. 3,371,114 and 3,484,466 and published European Patent Application No. 80301848.0. Finally, the sulfonyl isocyanate is coupled with an appropriate heterocyclic amine to prepare sulfonylurea herbicides as described in publications such as U.S. Pat. Nos. 4,127,405, 4,169,719 and 4,310,346 and in European Patent Application No. 81300956.0.

Examples of sulfonylurea herbicides which can be prepared from the intermediate sulfonyl-chlorides prepared according to this invention are:

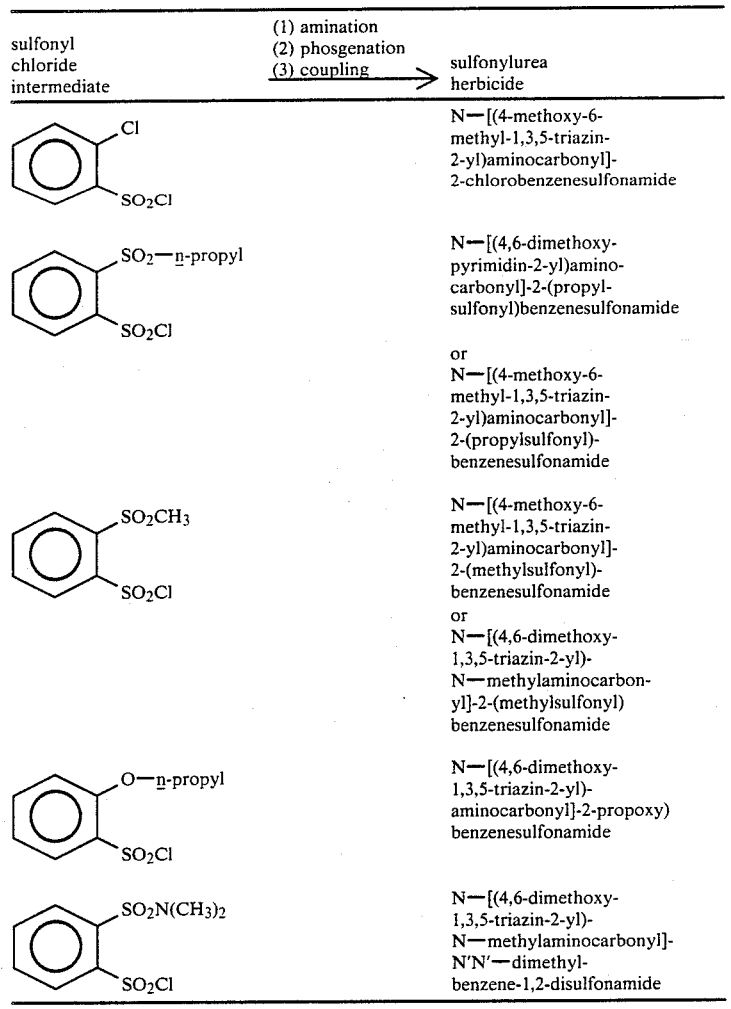

| sulfonyl chloride intermediate | (1) amination (2) phosgenation (3) coupling → | sulfonylurea herbicide |
|---|---|---|
| (2-Cl phenyl SO₂Cl) | | N—[(4-methoxy-6-methyl-1,3,5-triazin-2-yl)aminocarbonyl]-2-chlorobenzenesulfonamide |
| (2-SO₂-n-propyl phenyl SO₂Cl) | | N—[(4,6-dimethoxy-pyrimidin-2-yl)aminocarbonyl]-2-(propylsulfonyl)benzenesulfonamide<br>or<br>N—[(4-methoxy-6-methyl-1,3,5-triazin-2-yl)aminocarbonyl]-2-(propylsulfonyl)-benzenesulfonamide |
| (2-SO₂CH₃ phenyl SO₂Cl) | | N—[(4-methoxy-6-methyl-1,3,5-triazin-2-yl)aminocarbonyl]-2-(methylsulfonyl)-benzenesulfonamide<br>or<br>N—[(4,6-dimethoxy-1,3,5-triazin-2-yl)-N—methylaminocarbonyl]-2-(methylsulfonyl)benzenesulfonamide |
| (2-O-n-propyl phenyl SO₂Cl) | | N—[(4,6-dimethoxy-1,3,5-triazin-2-yl)aminocarbonyl]-2-propoxy)benzenesulfonamide |
| (2-SO₂N(CH₃)₂ phenyl SO₂Cl) | | N—[(4,6-dimethoxy-1,3,5-triazin-2-yl)-N—methylaminocarbonyl]-N'N'—dimethyl-benzene-1,2-disulfonamide |

In the following experimental descriptions, ODCB refers to ortho-dichlorobenzene and glc refers to gas-liquid chromatography. Nuclear magnetic resonance (NMR) absorptions are reported as parts per million downfield from tetramethylsilane, using abbreviations as follows: s, singlet; d, doublet; t, triplet; q, quartet; m, multiplet.

EXAMPLE 1

Reaction of ODCB with n-propyl mercaptide

Method A

A mixture of 100 g ODCB, 38 g of potassium propyl mercaptide and 5.7 g (15 weight %) of Carbowax ® 2000 polyethyleneglycol (available from Union Carbide) were heated at reflux under nitrogen for 2 hours, during which the temperature rose from 175° to 195° C. and all solids dissolved. A glc analysis after 2 hours showed complete reaction. Upon cooling, some solids precipitated out and were removed by filtration. Glc analysis of the filtrate showed it to contain 49.7% by weight of o-chlorophenyl propyl sulfide, corresponding to an 83.5% yield. Fractional distillation of the filtrate gave 62.6 g (74%) of o-chlorophenyl propyl sulfide, b.p. 75° (0.7 mmHg).

NMR (CDCl₃): 6.8–7.5 (m, 4H); 1.6 (m, 2H); 2.85 (t, 2H); and 1.0 (t, 3H).

Method B

A run similar to that of method A, but using 5.8 g of Carbowax ® 300 polyethyleneglycol (Union Carbide) and heating for 5 hours, produced a 90% yield (by glc analysis) of sulfide. The NMR spectrum and glc retention time of the product were identical to those of the product obtained by method A.

Method C

A mixture of 118 g of ODCB, 40 g of 85% potassium propyl mercaptide, and 6 g of linear polyether containing 63 mole % ethylene oxide and 37 mole % tetrahydrofuran monomer units, average molecular weight 1615, was heated at reflux overnight. After cooling and filtration to remove solids, the filtrate was stripped of solvent in vacuo. A quantitative glc analysis revealed an 85% yield of o-chlorophenyl propyl sulfide.

Using methyl mercaptide instead of n-propyl mercaptan, the procedures of this example can also be used to produce o-chlorophenyl methyl sulfide.

To illustrate the effect of the catalyst on this reaction, a mixture of 147 g of ODCB and 43 g potassium methyl mercaptide, in the absence of catalyst, was stirred and heated at 95°–100° for one hour. At the end of this period, the formation of o-chlorophenyl methyl sulfide was barely detectable (0.002 area %) by GLC. In strong contrast, when Carbowax ® 300 polyethyleneglycol (18 wt. % based on the mercaptide salt) was included from the beginning of the reaction, the sulfide product was present in 44 area % after thirty minutes and 47 area % after sixty minutes at which point the reaction was substantially complete. A similar result was obtained with Carbowax ® 350 polyethyleneglycol.

EXAMPLE 2 o-Bis-propylthiobenzene: Reaction of o-chlorophenyl propyl sulfide with potassium propyl mercaptide A solution of 215 g of 61.5 weight % of o-chlorophenyl propyl sulfide in o-dichlorobenzene (ODCB) was combined with 222.8 g of 85% potassium propyl mercaptide, 200 ml of xylene, 45 g of Carbowax ® 350, polyethyleneglycol (Union Carbide), and 20 ml of propyl mercaptan, and heated at reflux for 96 hours. The liquid temperature of the refluxing mixture, initially at 137° C., rose to 168° after 64 hours, and to 198° C. after 86 hours. The dark solution was cooled, diluted with 300 ml of toluene, and washed with water to remove inorganic salts. The organic phase was dried ($MgSO_4$) and fractionally distilled to give 48.6 g of recovered o-chlorophenyl propyl sulfide and 129.6 g (56.4%) of ortho-bis-propylthiobenzene, b.p. 100°–105° C. (0.06 mmHg).

NMR ($CDCl_3$): 6.9–7.3 (m, 4H); 2.85 (t, 4H); 1.70 (center of m, 4H); and 1.00 (t, 6H).

EXAMPLE 3

Reaction of 1,2,3-Trichlorobenzene with t-butyl mercaptide a. A mixture of 45.4 g (0.25 mole) of 1,2,3-trichlorobenzene, 31.3 g of 89.4% potassium hydroxide (0.50 mole), 13 g of Carbowax ® 400 polyethyleneglycol (Union Carbide) and 125 ml of t-butyl mercaptan was heated at reflux (80°–82° C.) with good stirring, and water produced by mercaptide formation was removed by co-distillation with t-butyl mercaptan and collected in a Dean-Stark trap. After 16 hours, excess t-butyl mercaptan was allowed to distill from the reaction mixture until the liquid temperature reached 95° C. Water was added to the mixture along with 100 ml of toluene. The organic layer was removed, dried ($MgSO_4$), and fractionally distilled to give about 45 g of (A) two isomeric dichloro-t-butylthiobenzenes, b.p. 90° (0.3 mmHg) (about 60% 2,6-dichloro-t-butylthiobenzene) and 10 g of (B) two isomeric chloro-bis-t-butylthiobenzenes, b.p. 112° (0.5 mmHg) (about 75% 3-chloro-1,2-bis-t-butylthiobenzene and about 25% 2-chloro-1,3-bis-t-butylthiobenzene. By allowing the reaction temperature to increase through removal of t-butyl mercaptan, the proportion of bis-t-butylthiobenzene (B) can be increased. Overall yields in this case are around 75% because of some decomposition at the higher temperatures.

NMR ($CDCl_3$): (A) 6.9–7.6 (m, 3H); and 1.31 (s) and 1.38 (s) (total 9H). (B) 7.18–7.65 (m, 3H); and 1.32 and 1.34 (s, 18H).

b. A second reaction of 1,2,3-trichlorobenzene with t-butyl mercaptide, not using catalyst, was run. In this reaction, 1,2,3-trichlorobenzene, potassium hydroxide and t-butyl mercaptan were combined in the amounts stated in paragraph (a) and heated at reflux with stirring.

In this reaction, the rate of water removal in the absence of catalyst was very much slower than in the earlier reaction in the presence of catalyst:

| With Catalyst | | Without Catalyst | |
|---|---|---|---|
| Time, hrs. | $H_2O$, mL | Time, hrs. | $H_2O$, mL |
| 1.75 | 3.5 | 1.5 | 0.2 |
| 3.75 | 6.0 | 3.0 | 0.5 |
| 6.50 | 9.5 | 4.5 | 0.8 |
| | | 27.0 | 4.6 |

In the absence of catalyst, the rate of formation of thioether was so slow as to be negligible in contrast to the earlier run with catalyst in which thioether formation was substantial in the early stages of the reaction.

| With Catalyst | | | Without Catalyst | | |
|---|---|---|---|---|---|
| Time hrs. | Thioethers, GC Area % | | Time hrs. | Thioethers, GC Area % | |
| | Isomer A | Isomer B | | Isomer A | Isomer B |
| 2.5 | 4.95 | 4.02 | 1.5 | 0 | 0 |
| 3.5 | 23.3 | 17.0 | 3.0 | 0 | 0 |
| 6.75 | 25.9 | 19.1 | 4.5 | 0 | 0 |
| | | | 28.0 | 0.19 | 0.16 |

(Isomer A = 2,6-dichloro-t-butylthiobenzene;
Isomer B = 2,3-dichloro-t-butylthiobenzene)

Clearly, in the absence of polyethyleneglycol catalyst, this reaction does not proceed to any significant degree. Addition of the catalyst causes a dramatic increase in rate of formation of potassium t-butyl mercaptide and in reaction of the latter with 1,2,3-trichlorobenzene to produce thioether.

EXAMPLE 4

Reaction of ODCB with sodium hydrosulfide

A mixture of 8 g (0.11 mole) of sodium hydrosulfide monohydrate, 3 g of Carbowax ® 400 polyethyleneglycol (Union Carbide), 35 ml of toluene, and 100 ml of diethyleneglycol was heated at reflux until all of the water of hydration was removed as the toluene azeotrope. There was added 14.7 g (0.1 mole) of ODCB, and the solution was heated at 150°–160° for 16 hours. The temperature was raised to 210° for 2 hours, and o-chlorothiophenol was identified in the solution by glc through comparison of its retention time with that of authentic material.

EXAMPLE 5

Conversion of o-chlorophenyl propyl sulfide to o-chlorophenyl propyl sulfone

Method A

To the ODCB solution from Example 1, method A above, containing 18.7 g of o-chlorophenyl propyl sulfide, was added 10 g of glacial acetic acid and 0.2 g sulfuric acid. Addition of 15 g of 50% aqueous $H_2O_2$ was accomplished over a 3 minute period. An exotherm raised the temperature to 94° C. within 20 minutes. After 1 hour, the reaction was heated to 105° C. for another hour. Glc analysis shows quantitative conversion to the title sulfone.

Method B

To a solution of 9.33 g of o-chlorophenyl propyl sulfide and 0.4 g $H_2SO_4$ in 40 ml of glacial acetic acid was added 8.25 g of 50% aqueous $H_2O_2$. Cooling in an ice bath was required to control the exotherm after the first portions raised the temperature to 40° C. After ca. half the peroxide was added no further exotherm was noted. The solution was stirred at ambient temperature overnight followed by heating to 80° C. for 15 minutes. The reaction mixture was quenched with water, extracted with methylene chloride, and the organic layer dried (MgSO4). Removal of the solvent in vacuo provided 10.9 g (99.8%) of the o-chlorophenyl propyl sulfone as an oil whose NMR spectrum and glc retention time were identical to those obtained for an authentic sample.

Method C

Chlorox ® (150 g of 5.25% aqueous sodium hypochlorite) was added dropwise with rapid stirring to a solution of 9.33 g of o-chlorophenyl propyl sulfide and 0.5 g tetra-n-butylammonium bisulfate in 65 ml of ethyl acetate over a 9 minute period. After stirring at ambient temperature overnight a glc analysis showed no sulfide remaining. Separation of layers, drying (MgSO4), and removal of solvent in vacuo provided 10.54 g (96.5%) of the sulfone as a colorless oil whose glc retention time and NMR spectrum were identical to those of the product obtained by method A.

By applying the procedures of this example to o-chlorophenyl methyl sulfide, o-chlorophenyl methyl sulfone is produced.

EXAMPLE 6

Oxidative chlorination of o-chlorophenyl propyl sulfide to o-chlorophenylsulfonyl chloride Chlorine (509 g) was added over 3.4 hours to a mixture of 179 g of o-chlorophenyl propyl sulfide and 38 g of water while keeping the temperature at 40°–50° C. After the addition was complete, the reaction mixture was held at 50° C. for an additional hour. After cooling, a quantitative glc analysis revealed an 82% yield of o-chlorophenylsulfonyl chloride.

EXAMPLE 7

Conversion of o-chlorophenyl propyl sulfone to o-propylthiophenyl propyl sulfone Method A Propanethiol (15.5 ml, 0.17 mole) was added dropwise over a period of 10 minutes to a mixture of 21.85 g (0.1 mole) o-chlorophenyl propyl sulfone and 10.9 g (0.17 mole) KOH (broken into small pieces) in 100 ml of toluene. After a slight exotherm and apparent precipitation of the mercaptide salt, 6.5 g of Carbowax ® 350 polyethyleneglycol (Union Carbide) was added to the colorless mixture, immediately turning it yellow. After heating a reflux for 4 hours a glc analysis showed no remaining starting sulfone. During reflux ca. 3 ml of water was collected in a Dean-Stark trap.

Water was added to the cooled reaction mixture, the layers were separated, and the organic layer was washed three times with water and dried (MgSO4). Removal of the solvent in vacuo provided 23.82 g (92.3%) of the title compound as an oil:

NMR (CDCl3): 8.1–7.0 (m, 4H); 3.45 (t, 2H); 3.0 (t, 2H), 2.1–1.4 (m, 4H); and 1.2–0.8 (overlapping t's, 6H).

Method B

A slurry of 10.93 g of the chlorosulfone and 6.7 g of 85% pure potassium propyl mercaptide in 20 ml of o-dichlorobenzene was heated at 100° C. for 7 hours, after which a glc analysis showed no remaining chlorosulfone, indicating a quantitative conversion to the title sulfide-sulfone.

Method C

Propanethiol (1.0 mol) was added dropwise via syringe to a mixture of 2.18 g of o-chlorophenyl propyl sulfone, 15 ml toluene, 0.2 g tetra-n-butylammonium bromide, and 15 ml of 50% NaOH. The temperature rose as high as 34° during this addition. The reaction was approximately 80% complete (by glc) after 40 minutes but was stirred overnight at ambient temperature, whereupon a glc analysis showed quantitative conversion to the title compound.

Applying the procedures of this example to o-chlorophenyl methyl sulfone and methyl mercaptan, o-methylthiophenyl methyl sulfone is produced.

EXAMPLE 8

Oxidative chlorination of o-methylthiophenyl methyl sulfone

Chlorine (27 g) was introduced into a slurry of 13.2 g of the title sulfide in 50 ml of glacial acetic acid and 3 ml of water in a 250 ml morton flask equipped with a mechanical stirrer and dry ice condenser. The reaction was exothermic at first but later required heating to maintain a temperature of 50°–60° C. After the addition was complete, the mixture was kept at 60°–70° C. for an additional hour, during which time solids started to precipitate out. Upon cooling and quenching the reaction with water, o-(methylsulfonyl)-phenylsulfonyl chloride was obtained as white crystals. Filtration, water washing, and air drying provided 13.9 g (84%) of the sulfonyl chloride, m.p. 113°–135° C.

NMR (DMSO-$d_6$): 8.3 (m, 2H); 7.9 (m, 2H); and 3.6 (s, 3H).

EXAMPLE 9

Oxidative chlorination of o-propylthiophenyl propyl sulfone

Chlorine (30 g) was introduced into a mixture of 18.66 g of the title sulfide and 3.25 l ml of $H_2O$ in 55 ml of glacial acetic acid over 90 minutes. The initial exotherm was no longer noticeable after ca. half the chlorine was added, and heating was required to maintain the temperature at 50°–60° C. After the addition was complete, the mixture was heated an additional 2 hours at 50°–60° C. After cooling and quenching with cold water, o-(propylsulfonyl)phenylsulfonyl chloride was obtained by filtration. Washing with water and cold ligroin provided 14.12 g (69%) of the sulfonyl chloride as white crystals, m.p. 74°–77° C.

EXAMPLE 10

Mercaptidation of 3,5-dichloropyridine

A mixture of 14.8 g of 3,5-dichloropyridine, 50 ml of xylene, 11 g of potassium propyl mercaptide, and 2 of Carbowax ® 2000 polyethyleneglycol (Union Carbide) was heated at reflux for 3 hours. After cooling to 70°, another 2 g of the mercaptide was added and heating was continued for another hour. The reaction mixture was then cooled and filtered to remove precipitated salts. The filtrate was stripped of solvent in vacuo to obtain 20.7 g of crude product which was distilled to provide 14.4 g (77%) of 3-chloro-5-n-propylthiopyridine as an oil, bp 95°–97° (1.5 mm).

NMR (CDCl3): 8.2–8.4 (m, 2H); 7.55 (t, 1H, J=3 Hz); 2.9 (t, 2H, J=7 Hz); 1.6 (m, 2H, J=7 Hz); and 1.0 (t, 3H, J=7 Hz).

EXAMPLE 11

Mercaptidation of 3,4-dibromothiophene

A mixture of 50 g of 3,4-dibromothiophene, 30 g of 85% potassium propyl mercaptide and 4.5 g of Carbowax® 2000 in 50 ml of xylene was heated at reflux for 18 hours. The reaction was cooled, an additional 9 g of the mercaptide was added, and refluxing was continued for an additional 31 hours. After cooling, the mixture was filtered and the filtrate distilled to provide 10.6 g (21.3%) of 3-bromo-4-(propylthio)thiophene, bp 91°–102° C. (1.4 mm).

NMR (CDCl$_3$): 7.12 (q, 2H, J=4 Hz); 2.8 (t, 2H, J=7 Hz); 1.65 (m, 2H); and 1.0 (t, 3H, J=7 Hz).

EXAMPLE 12

De-alkylation of an alkyl phenyl sulfide

A solution of 1.0 g of o-chlorophenyl t-butyl sulfide to 10 ml of xylene containing a trace of p-toluenesulfonic acid was heated at reflux and periodically examined by glc. The starting sulfide gradually disappeared, and a new component with the same glc retention time as that of authentic o-chlorophenyl mercaptan appeared. After six hours, the conversion to o-chlorobenzenethiol was complete. The rate of formation of the mercaptan can be increased by using higher concentrations of p-toluenesulfonic acid.

EXAMPLE 13

Chlorobenzenedithiols

A solution of 14.5 g (0.05 mole) of isomeric chloro-bis-t-butylthiobenzenes (containing 3-chloro-1,2-bis-t-butylthiobenzene and 2-chloro-1,3-bis-t-butylthiobenzene in the ratio 2.9:1) and 1.5 g of p-toluenesulfonic acid in 150 ml of xylene was heated at reflux for 16 hours, and the solution was fractionally distilled without further treatment. After removal of the solvent, there was obtained 7.2 g (81%) of mixed chlorobenzenedithiols, b.p. 90°–93° (0.8 mmHg).

NMR (CDCl$_3$): 1. 3-chloro-1,2-benzenedithiol (72%) 6.5–7.5 (m, 3H); 4.42 (s, 1H); and 3.65 (s, 1H). 2. 2-chloro-1,3-benzenedithiol (28%) 6.5–7.5 (m, 3H); and 3.80 (s, 2H).

What is claimed is:

1. A process for preparing a sulfonyl chloride of the formula:

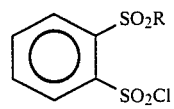

where R is lower alkyl, comprising
 (a) contacting ortho-dichlorobenzene with an anionic nucleophile in the form of a salt of the formula M$^+$SR$^-$ where M is an alkali metal in the presence of an acyclic polyethyleneglycol catalyst to produce the compound

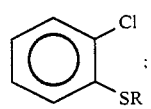

(b) oxidizing the product of step (a) to produce the compound

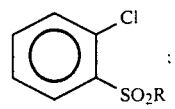

(c) contacting the product of step (b) with a salt of the formula M$^+$SR$_1^-$ where M is an alkali metal and R$_1$ is lower alkyl to produce the compound

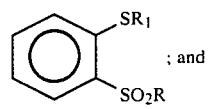

(d) chlorinating the product of step (c) in the presence of water to prepare the desired sulfonyl chloride.

2. The process of claim 1 where the product of step (a) is oxidized by contacting it with either (i) acidic hydrogen peroxide or (ii) alkaline sodium hypochlorite.

3. A process for preparing a sulfonyl chloride of the formula

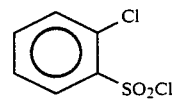

comprising
 (a) contacting ortho-dichlorobenzene with an anionic nucleophile in the form of a salt of the formula M$^+$SR$^-$ where R is lower alkyl and M is an alkali metal in the presence of an acyclic polyethyleneglycol catalyst to produce the compound

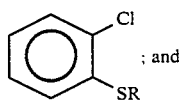

(b) chlorinating in the presence of water the product of step (a) to prepare the desired sulfonyl chloride.

4. A process for preparing a sulfonyl chloride of the formula

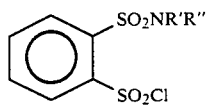

where R' and R'' are independently lower alkyl, comprising
 (a) contacting ortho-dichlorobenzene with an anionic nucleophile in the form of a salt of the formula M$^+$SR$^-$ where R is lower alkyl and M is an alkali metal in the presence of an acyclic polyethyleneglycol catalyst to produce the compound

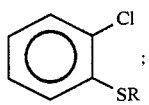

(b) chlorinating the product of step (a) in the presence of water to prepare the sulfonyl chloride

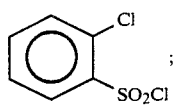

(c) contacting the sulfonyl chloride prepared in step (b) with a dialkylamine of the formula NHR'R" where R' and R" are independently lower alkyl to prepare a compound of the formula

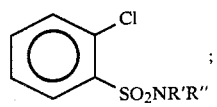

(d) contacting the product of step (c) with a salt of the formula $M^+SR^-$, where M and R are as previously defined, to produce the compound

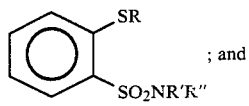

(e) chlorinating the product of step (d) in the presence of water to produce the desired product.

5. A process for preparing a sulfonyl chloride of the formula

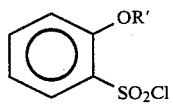

where R' is lower alkyl, comprising either (i)
(a) contacting ortho-dichlorobenzene with an anionic nucleophile in the form of a salt of the formula $M^+SR^-$ where R is lower alkyl and M is an alkali metal in the presence of an acyclic polyethyleneglycol catalyst to produce the compound

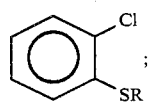

(b) contacting the product of step (i)(a) with alkoxide —OR', to prepare the compound

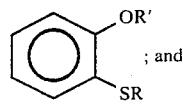

(c) chlorinating the product of step (i)(b) in the presence of water to produce the desired compound;

(ii)
(a) contacting ortho-dichlorobenzene with a salt of the formula $M^+OR'^-$ in the presence of an acyclic polyethyleneglycol catalyst to produce the compound

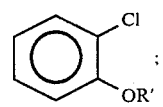

(b) contacting the product of step (ii)(a) with a salt of the formula $M^+SR^-$ in the presence of an acyclic polyethyleneglycol catalyst to produce the compound

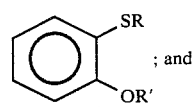

(c) chlorinating the product of step (ii)(b) in the presence of water to produce the desired product.

6. A process for preparing a thiophenol of the formula

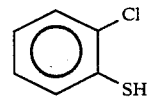

comprising (a) contacting ortho-dichlorobenzene with an anionic nucleophile in the form of a salt of the formula $M^+SR^-$ where R is a secondary or tertiary lower alkyl and M is an alkali metal in the presence of an acyclic polyethyleneglycol catalyst to produce the compound

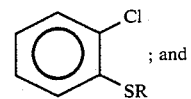

(b) heating the product of step (a) with a strong acid.

7. A process for preparing a bis-thiophenol of the formula

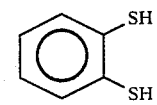

comprising (a) contacting ortho-dichlorobenzene with an anionic nucleophile in the form of a salt of the formula M+SR− where R is lower alkyl and M is an alkali metal in the presence of an acyclic polyethyleneglycol catalyst to produce the compound

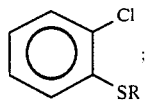

(b) contacting the product of step (a) with an anionic nucleophile in the form of a salt of the formula M+SR$_1$− where R$_1$ is lower alkyl and M is an alkali metal in the presence of an acyclic polyethyleneglycol catalyst to produce the compound

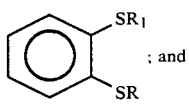 ; and (e) either (i) heating the product of step (b) with a strong acid when R and R$_1$ are secondary or tertiary alkyl, or (ii) contacting the product of step (b) with sodium metal in liquid ammonia, followed by acidification; or (iii) contacting the product of step (b) with mercaptide, followed by acidification.

8. The process of claim 7 where either the bis-thioether

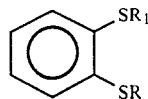

or the bis-thiophenol

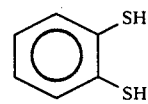

are chlorinated in the presence of water to prepare a disulfonyl chloride of the formula

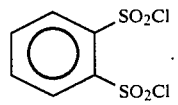

* * * * *

UNITED STATES PATENT AND TRADEMARK OFFICE
CERTIFICATE OF CORRECTION

PATENT NO. : 4,683,091
DATED : JULY 28, 1987
INVENTOR(S) : ALDEN D. JOSEY

It is certified that error appears in the above-identified patent and that said Letters Patent is hereby corrected as shown below:

In Claim 5, at column 24, line 10, after paragraph (c) add "or" after -- pound; -- and at line 11, before "(a)" "(iii)" should read --(ii)--.

Signed and Sealed this

Twenty-second Day of March, 1988

Attest:

DONALD J. QUIGG

Attesting Officer

Commissioner of Patents and Trademarks